United States Patent [19]

Miura et al.

[11] Patent Number: 5,760,053
[45] Date of Patent: Jun. 2, 1998

[54] γ-DIKETONE COMPOUNDS WITH INHIBITORY ACTIVITY AGAINST PLATELET AGGREGATION

[75] Inventors: Tomoaki Miura; Eiki Shitara; Shokichi Ohuchi; Kiyoaki Katano, all of Kanagawa-ken, Japan

[73] Assignee: Meiji Seika Kabushiki Kaisha, Tokyo, Japan

[21] Appl. No.: 656,245

[22] PCT Filed: Oct. 6, 1995

[86] PCT No.: PCT/JP95/02057

§ 371 Date: Sep. 5, 1996

§ 102(e) Date: Sep. 5, 1996

[87] PCT Pub. No.: WO96/11180

PCT Pub. Date: Apr. 18, 1996

[30] Foreign Application Priority Data

Oct. 7, 1994 [JP] Japan .................... 6-243736
Oct. 20, 1994 [JP] Japan .................... 6-255333

[51] Int. Cl.$^6$ .................... A61K 31/44; C07D 495/04
[52] U.S. Cl. .................... 514/301; 546/114
[58] Field of Search .................... 546/114; 514/301

[56] References Cited

FOREIGN PATENT DOCUMENTS 0656348  6/1995  European Pat. Off. .

*Primary Examiner*—Alan L. Rotman
*Attorney, Agent, or Firm*—Wenderoth, Lind & Ponack, L.L.P.

[57] ABSTRACT

A γ-diketone compound represented by the following formula (I) and a pharmaceutically acceptable salt and solvate thereof having platelet aggregation inhibitory activity is disclosed:

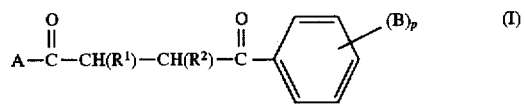

wherein B is $-Z-(CH_2)_q COOR^7$ and A is the following group (II) or (III):

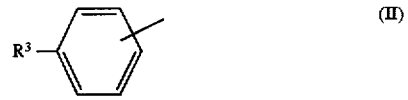

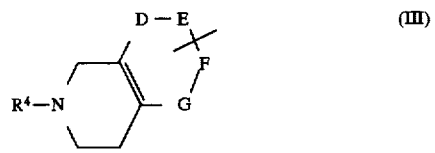

9 Claims, No Drawings

# γ-DIKETONE COMPOUNDS WITH INHIBITORY ACTIVITY AGAINST PLATELET AGGREGATION

CROSS-REFERENCE

This application is a 371 of PCT/JP95/02057 filed Oct. 6, 1995.

BACKGROUND OF THE INVENTION

1. Field of Invention

The present invention relates to γ-diketone compound derivatives having inhibitory activity against platelet aggregation and pharmaceutical compositions useful for the treatment and prevention of thrombotic diseases.

2. Background Art

Cardiovascular diseases are increased along with the change of dietary habits and the increase of advanced ages. Almost fifty percent of these diseases may be caused by thrombus.

Platelets in plasma are mainly associated with the formation of thrombus in organisms. For the purpose of the treatment and prevention of thrombotic diseases in clinical practice, there have been used a medicine which suppresses the functions of platelet or inhibits the aggregation of platelets, for example, aspirin which inhibits cyclooxygenase and ticlopidine which activates adenylcyclase.

In recent years, glycoproteins on platelet membrane have been progressively studied. As a result, it has been elucidated that the membrane glycoprotein called GPIIb/IIIa is a receptor of fibrinogen. This has therefore led to the expectation that a GPIIb/IIIa antagonist would become an inhibitor of platelet aggregation having a novel action mechanism effectively used for the treatment and prevention of the thrombotic diseases (Trends in Pharmacological Science, 13, 413, 1992).

The compounds as the GPIIb/IIIa antagonist include, for examples, monoclonal antibodies (Ann. N.Y. Acad. Sci., 614, 193, 1991), tripeptide derivatives comprising arginine-glycine-aspartic acid (J. Med. Chem., 35, 2040, 1992), amidinophenyl derivatives (J. Med. Chem., 35, 4393, 1992; Japanese Patent Laid-Open Publication Nos. 264068/1992, 334351/1992, EP-A-483667, EP-A-502536, EP-A-525629, EP-A-529858, EP-A-537980, WO-9307867 and WO-9402472), tyrosine derivatives (J. Med. Chem., 35, 4640, 1992), and piperidine derivatives (EP-A-512831, EP-A-540334 and EP-A-578535).

Further, for γ-diketone compounds, compounds having a peptide bond are known in the art (Japanese Patent Laid-Open Publication No. 235853/1990, WO09307867 and the like), whereas no compounds free from a peptide bond are known in the art. It is expected that such compounds not having any peptide bond are less likely to be metabolized by peptidases in vivo. Therefore, they are potentially promissing compounds which can offer prolonged duration of efficacy.

On the other hand, the development of a drug, not having side effects such as hemorrhage and with a highly selective function, as a therapeutic or preventive agent of thrombotic diseases has been desired in the art.

SUMMARY OF THE INVENTION

The present inventors have now found that a certain kind of a compound becomes a GPIIb/IIIa antagonist.

Thus, an object of the present invention is to provide novel compounds having inhibitory activity against the aggregation of platelets.

Another object of the present invention is to provide a pharmaceutical composition comprising a novel compound having the above effect.

Further object of the present invention is to provide a therapeutic or preventive method of thrombotic diseases which comprises administering a novel compound having the above activity.

Further object of the present invention is to provide the use of the novel compound having the above activity for preparing a pharmaceutical composition used for the therapy or prevention of thrombotic disorders. The γ-diketone compound according to the present invention is represented by the formula (I):

$$A-\overset{O}{\underset{\|}{C}}-CH(R^1)-CH(R^2)-\overset{O}{\underset{\|}{C}}-\underset{\phantom{x}}{\text{(benzene ring)}}(B)_p \quad (I)$$

wherein

R$^1$ and R$^2$ which may be the same or different is hydrogen; lower alkyl in which at least one hydrogen atom may be substituted by hydroxyl, halogen, amino, carboxyl, lower alkoxy, lower alkylamino, or lower alkoxycarbonyl; phenyl in which at least one hydrogen atom of the phenyl may be substituted by hydroxyl, halogen, amino, carboxyl, lower alkoxy, lower alkylamino, lower alkoxycarbonyl, or halo-lower alkyl; or phenyl-lower alkyl in which at least one hydrogen atom of the phenyl may be substituted by hydroxyl, halogen, amino, carboxyl, lower alkoxy, lower alkylamino, lower alkoxycarbonyl, or halo-lower alkyl;

A is the following group (II) or (III):

$$R^3-\underset{\phantom{x}}{\text{(benzene ring)}} \quad (II)$$

$$R^4-N\underset{\phantom{x}}{\text{(ring with D-E, F, G)}} \quad (III)$$

wherein

R$^3$ is amidino or amino-substituted lower alkyl;

R$^4$ is hydrogen atom; lower alkyl in which at least one hydrogen atom may be substituted by hydroxyl, halogen, amino, or lower alkylamino; or amidino;

D, E, F, and G which may be the same or different is —CR$^5$=, —CR$^5$R$^6$—, —N=; —NR$^5$—, —O—, —S—, —(CO)—, or a bond wherein R$^5$ and R$^6$ which may be the same or different is hydrogen or lower alkyl;

B is —Z—(CH$_2$)$_q$COOR$^7$ wherein Z is —O— or a bond, R$^7$ is hydrogen, lower alkyl, or an ester residue which can be removed under physiological conditions and q is an integer of 1 to 4; and p is an integer of 1 to 3; and a pharmaceutically acceptable salt and solvate thereof.

The platelet aggregation inhibitor according to the present invention comprises as an effective ingredient a compound represented by the general formula (I) or a pharmaceutically acceptable salt and solvate thereof.

The compound according to the present invention has excellent inhibitory activity against platelet aggregation and, further, is free from side effects derived from hemorrhage and lack of selectivity for inhibitory action. Therefore, the present invention can provide a platelet aggregation inhibitor which is safe to the human body.

DETAILED DESCRIPTION OF THE INVENTION

Compound of the general formula (I)

The term "lower alkyl" as a group or a portion of a group used herein means a straight or branched alkyl chain having 1 to 6, preferably 1 to 4 carbon atoms. The term halogen atom means fluorine, chlorine, bromine or iodine. Furthermore, the term "haloalkyl" means an alkyl group in which one or more hydrogen atoms are substituted by halogen atoms.

In the general formula (I), $R^1$ and $R^2$ are a hydrogen atom, a lower alkyl group, a phenyl group or a phenyl-lower alkyl group. At least one hydrogen atom of this lower alkyl group may be substituted. Preferred examples of this substituent include a hydroxyl group, a halogen atom (preferably, chlorine, bromine or fluorine), an amino group, a carboxyl group, a lower alkoxy group (preferably, methoxy, ethoxy, n-propoxy or iso-propoxy), a lower alkylamino group (preferably, methylamino, ethylamino, propylamino, dimethylamino or diethylamino), or a lower alkoxycarbonyl group (preferably, methoxycarbonyl, ethoxycarbonyl, n-propoxycarbonyl or iso-propoxycarbonyl). Furthermore, at least one hydrogen atom of the phenyl group may be substituted. Specific examples of this substituent include a hydroxyl group, a halogen atom (preferably, chlorine, bromine or fluorine), an amino group, a carboxyl group, a lower alkoxy group (preferably, methoxy, ethoxy, n-propoxy or iso-propoxy), a lower alkylamino group (preferably, methylamino, ethylamino, propylamino, dimethylamino or diethylamino), a lower alkoxycarbonyl group (preferably, methoxycarbonyl, ethoxycarbonyl, n-propoxycarbonyl or iso-propoxycarbonyl), or a halo-lower alkyl group (preferably, trifluoromethyl or trifluoroethyl).

In addition, at least one hydrogen atom of the phenyl group in the phenyl-lower alkyl group (preferably, benzyl, 2-phenylethyl or 3-phenylpropyl) may be substituted. Preferred examples of this substituent include a hydroxyl group, a halogen atom (preferably, chlorine, bromine or fluorine), an amino group, a carboxyl group, a lower alkoxy group (preferably, methoxy, ethoxy, n-propoxy or isopropoxy), a lower alkylamino group (preferably, methylamino, ethylamino, propylamino, dimethylamino or diethylamino), a lower alkoxycarbonyl group (preferably, methoxycarbonyl, ethoxycarbonyl, n-propoxycarbonyl or isopropoxycarbonyl), or a halo-lower alkyl group (preferably, trifluoromethyl or trifluoroethyl).

In the formula (II), the amino-substituted lower alkyl represented by $R^3$ is most preferably aminomethyl.

In the formula (III), $R^4$ is a hydrogen atom or a lower alkyl or amidino group. At least one hydrogen atom of the lower alkyl group may be substituted. Specific examples of the substituent include a hydroxyl group, a halogen atom (preferably, chlorine, bromine or fluorine), an amino group, or a lower alkylamino (preferably, methylamino, ethylamino, propylamino, dimethylamino or diethylamino).

The group represented by the formula (II) and the carbonyl group may be bonded to each other at any position without limitation, with the bonding at the 4-position to $R^3$ being preferred.

Examples of the group (III) include that D or G is —$NR^5$—, —O— or —S— and the other represents a bond with both E and F representing —$CR^5$=. Specific preferred examples of the formula (III) include 4,5,6,7-tetrahydrothieno[3,2-c]pyridin-2-yl or 3-yl, 4,5,6,7-tetrahydrothieno[2,3-c]pyridin-2-yl or 3-yl, 1-methyl-4,5,6,7-tetrahydropyrrolo[3,2-c]pyridin-2-yl or 3-yl, 1-methyl-4,5,6,7-tetrahydropyrrolo[2,3-c]pyridin-2-yl or 3-yl, 4,5,6,7-tetrahydrofuro[3,2-c]pyridin-2-yl or 3-yl, and 4,5,6,7-tetrahydrofuro[2,3-c]pyridin-2-yl or 3-yl.

In the group —Z—$(CH_2)_q COOR^7$ as B in the general formula (I), Z represents an oxygen atom or a bond with Z being preferably an oxygen atom. Further, q is preferably an integer of 1 or 2. Preferred examples of lower alkyls as $R^7$ include methyl, ethyl, n-propyl, iso-propyl, or n-, iso-, sec-, or t-butyl. $R^7$ may represent an ester residue which can be removed under physiological conditions. Specific examples of such ester residues include pivaloyloxymethyl, 1-(cyclohexyloxycarbonyloxy) ethyl, (5-methyl-2-oxo-1,3-dioxol-4-yl)methyl.

The compound according to the present invention can be in the form of a salt. Such a salt includes a pharmacologically acceptable non-toxic salt. Preferred examples of the salt include inorganic salts such as a sodium salt, a potassium salt, a magnesium salt and a calcium salt, acid addition salts such as a trifluoroacetate salt, a hydrochloride salt, a sulfate salt, an oxalate salt, a methanesulfonate salt, and a citrate salt, and amino acid salts such as a glutamate salt and an aspartate salt.

The compound according to the present invention can be in the form of a solvate. The solvate preferably includes a hydrate and an ethanolate.

Preparation of the Compound represented by the Formula (I)

The compound according to the present invention can be prepared by the following processes.

Protective groups for an amino group which are generally used in peptide synthesis may be used in the following processes. Preferred examples of the protective group include t-butoxycarbonyl, benzyloxycarbonyl, 4-methoxybenzyloxycarbonyl, 2,2,2-trichloroethoxycarbonyl, trifluoroacetyl, allyloxycarbonyl and trityl. Furthermore, protective groups for a carboxyl group which are generally used in peptide synthesis may be used in the following processes. Preferred examples of the protective group include methyl, ethyl, t-butyl, benzyl, 4-methoxybenzyl, 4-nitrobenzyl, allyl and benzhydryl.

Process (1)

A compound of the formula (I) wherein A represents the group (III) can be prepared by the following reaction.

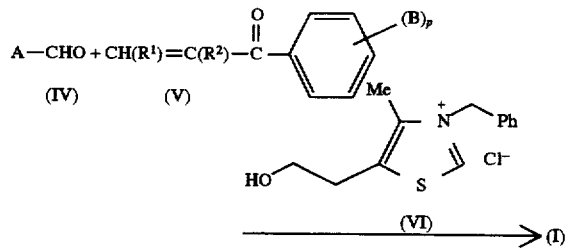

A compound represented by the general formula (IV), wherein A is as defined above, provided that $R^4$ in A is as defined above and, in addition, may represent a protective group for the amino group, is reacted with a compound represented by the general formula (V), wherein $R^1$, $R^2$, B, and p are as defined above, provided that $R^7$ in B is as defined above and, in addition, may represent a protective group for the ester group, in an inert solvent in the presence of a catalyst (VI) and a base at 0° to 180° C., preferably at 10° to 100° C., for 0.5 to 24 hr, preferably for 1 to 10 hr, and, thereafter, optionally subjected to deprotection, thereby giving the compound represented by the formula (I).

The compound represented by the general formula (IV) may be prepared according to a process described in Japanese Patent Application No. 265273/1993, and the compound represented by the general formula (VI) may be prepared according to a process described in Synthesis, p. 379 (1975).

Process (2)

A compound of the formula (I) where A represents the group (II), wherein $R^3$ represents an amidino group, can be prepared using the compound of the formula (VII) as a starting material.

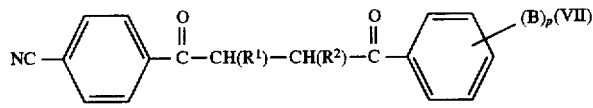

Specifically, a cyano compound represented by the general formula (VII), wherein $R^1$, $R^2$, p, and B are as defined above, provided that $R^7$ in B is as defined above and, in addition, may represent a protective group for the ester group, is reacted with hydrogen sulfide and triethylamine in pyridine to give a thioamide which is then methylated with methyl iodide in an inert solvent (preferably, acetone), further reacted with ammonium acetate or ammonium carbonate in an inert solvent (preferably, methanol) and optionally subjected to deprotection, thereby preparing a contemplated compound.

For a person having ordinary skill in the art, it would be apparent that, in the above production processes, the sequence of the reactions may be determined so that no side reaction occurs in a function group which does not participate in the reaction and that the functional group may be protected with a protective group suitable for preventing the progression of an unfavorable reaction.

Use of the compound/pharmaceutical composition

The compound according to the present invention inhibits the aggregation of platelets by inhibiting the binding of platelet membrane protein GPIIb/IIIa and fibrinogen. Thus, the compound according to the present invention and a pharmacologically acceptable salt thereof are effective in the treatment and prevention of thrombotic disorders caused by the aggregation of platelets, particularly cerebral infarction, myocardial infarction, angina pectoris or peripheral arteriocclusion.

A pharmaceutical composition comprising the compound according to the present invention or a pharmacologically acceptable salt thereof as an effective ingredient can be administered to human and non-human animal subjects through any one of routes such as oral or parenteral routes such as intravenous injection, intramuscular injection, subcutaneous administration, rectal administration or percutaneous administration.

Therefore, the pharmaceutical composition comprising as an effective ingredient the compound according to the present invention may be processed into suitable dosage forms depending on dosage routes, and can be specifically formed into preparations mainly including injections such as intravenous injection or intramuscular injection, oral preparations such as capsule, tablet, granule, powder, pill, grains or troche, rectal preparations, oily suppositories or aqueous suppositories.

These preparations can be prepared in the usual manners with conventional additives such as an excipient, a filler, a binder, a humidifier, a disintegrating agent, a surface active agent, a lubricant, a dispersant, a buffer, a preservative, a dissolution aid, an antiseptic agent, a flavoring agent, an analgesic agent or a stabilizer. The aforementioned acceptable and non-toxic additives include, for example, lactose, fructose, glucose, starch, gelatin, magnesium carbonate, synthetic magnesium silicate, talc, magnesium stearate, methyl cellulose or a salt thereof, gum arabic, polyethylene glycol, syrup, vaseline, glycerin, ethanol, propylene glycol, citric acid, sodium chloride, sodium sulfite and sodium phosphate.

The content of the compound according to the present invention in the pharmaceutical composition may vary depending on dosage forms. It, however, generally ranges from about 1 to 70% by weight, preferably from about 5 to 50% by weight of the total composition.

The dose is appropriately determined in consideration of the use, and the age, sex and severity of a patient. The dose is generally in the range from about 0.1 to 1,000 mg, preferably from 1 to 200 mg per day to an adult patient for the purpose of the treatment of thrombotic disorders. The dose may be administered in one or more portions per day.

EXAMPLES

Preparation 1

3,4-Bis(t-butoxycarbonylmethyloxy)benzaldehyde 3,4-Dihydroxybenzaldehyde (9.67 g) was dissolved in acetone (250 ml), and potassium carbonate (21.3 g) and t-butyl bromoacetate (24.6 ml) were added thereto. The resultant solution was stirred at room temperature, and, 2.5 hr after the initiation of stirring, t-butyl bromoacetate (2 ml) was further added to the reaction mixture, followed by stirring for 3.5 hr. Water was added to the reaction mixture, and acetone was then distilled off. The aqueous layer was extracted with ethyl acetate, the resultant organic layer was washed with water and dried over magnesium sulfate, and the solvent was distilled off. The residue thus obtained was purified by column chromatography on silica gel (500 g, chloroform:methanol=100:1) to give 25.4 g of the title compound (yield 99%).

$^1$H-NMR (CDCl$_3$) δ: 1.48 (9H, s), 1.49 (9H, s), 4.67 (2H, s), 4.70 (2H, s), 6.90 (1H, d, J=8.2 Hz), 7.35 (1H, d, J=2.0 Hz), 7.46 (1H, dd, J=2.0, 8.2 Hz), 9.84 (1H, s) EIMS (m/z): 366 (M$^+$)

Preparation 2

3,4-Bis(n-butoxycarbonylmethyloxy)benzaldehyde 3,4-Dihydroxybenzaldehyde (6.91 g), potassium carbonate (20.7 g), n-butyl chloroacetate (15.5 ml), and sodium iodide (2.25 g) were dissolved in dimethylformamide (100 ml), and the solution was treated in the same manner as in Preparation 1 to give 13.4 g of the title compound (yield 73%).

$^1$H-NMR (CDCl$_3$) δ: 0.91 (3H, t, J=7.5 Hz); 0.92 (3H, t, J=7.5 Hz), 1.29–1.42 (4H, m), 1.59–1.69 (4H, m), 4.21 (4H, t, J=6.7 Hz), 4.78 (2H, s), 4.81 (2H, s), 6.93 (1H, d, J=8.1 Hz), 7.38 (1H, d, J=1.7 Hz), 7.48 (1H, dd, J=1.7, 8.1 Hz), 9.84 (1H, s) EIMS (m/z): 366 (M$^+$)

Preparation 3

1,2-Bis(t-butoxycarbonylmethyloxy)-4-(3-hydroxy-1-propenyl)benzene

The compound (5.13 g) prepared in Preparation 1 was dissolved in tetrahydrofuran (40 ml). The solution was cooled to −30° C., and vinyl magnesium bromide (about 1.0M THF solution, 18.2 ml) was added thereto. The mixture was stirred at −25° to −30° C., and, one hr after the initiation of stirring, vinyl magnesium bromide (9.8 ml) was added thereto, followed by stirring for 30 min. An aqueous ammonium chloride solution (0.35M, 120 ml) was added to the reaction mixture, and tetrahydrofuran was distilled off. The aqueous layer was extracted with ethyl acetate, and the organic layer was washed with water, a saturated aqueous solution of sodium hydrogencarbonate, and water in that order, and dried over magnesium sulfate. The solvent was then distilled off, and the residue was purified by column chromatography on silica gel (300 g, chloroform—chloroform:methanol=50:1) to give 3.70 g of the title compound (yield 70%).

$^1$H-NMR (CDCl$_3$) δ: 1.47 (18H, s), 1.88 (1H, br s), 4.59 (2H, s), 4.60 (2H, s), 5.12 (1H, d, J=5.6 Hz), 5.18 (1H, dt, J=1.5, 10.3 Hz), 5.32 (1H, dt, J=1.5, 17.2 Hz), 5.94–6.04 (1H, m), 6.82 (1H, d, J=8.2 Hz), 6.87 (1H, d, J=1.8 Hz), 6.92 (1H, dd, J=1.8, 8.2 Hz), EIMS (m/z): 366 (M$^+$)

Preparation 4

1,2-Bis(n-butoxycarbonylmethyloxy)-4-(3-hydroxy-1-propenyl)benzene

The compound prepared in Preparation 2 was treated in the same manner as in Preparation 3 to give 3.18 g of the title compound (yield 40%).

$^1$H-NMR (CDCl$_3$) δ: 0.91 (3H, t, J=7.5 Hz), 0.92 (3H, t, J=7.5 Hz), 1.29–1.41 (4H, m), 1.58–1.67 (4H, m), 1.93 (1H, d, J=3.9 Hz), 4.18 (2H, t, J=6.7 Hz), 4.19 (2H, t, J=6.7 Hz), 4.71 (2H, s), 4.72 (2H, s), 5.10–5.15 (1H, m), 5.18 (1H, dt, J=1.4, 10.5 Hz), 5.32 (1H, dt, J=1.4, 17.2 Hz), 5.94–6.04 (1H, m), 6.86 (1H, d, J=8.1 Hz), 6.89–6.96 (2H, m) EIMS (m/z): 394 (M$^+$)

Preparation 5

1,2-Bis(t-butoxycarbonylmethyloxy)-4-(3-oxo-1-propenyl)benzene

Pyridinium chlorochromate (3.03 g), Molecular Sieves 4A (5.50 g) were suspended in dichloromethane (45 ml), and a solution of the compound (3.70 g), prepared in Preparation 3, in dichloromethane (45 ml) was added thereto. The mixture was stirred at room temperature for 1.5 hr. The reaction mixture was filtered through Florisil, and the filtrate was concentrated. The residue thus obtained was purified by column chromatography on silica gel (80 g, hexane:ethyl acetate=10:1–5:1) to give 1.59 g of the title compound (yield 43%).

$^1$H-NMR (CDCl$_3$) δ: 1.48 (9H, s), 1.49 (9H, s), 4.67 (2H, s), 4.68 (2H, s), 5.88 (1H, dd, J=1.7, 10.5 Hz), 6.42 (1H, dd, J=1.7, 16.9 Hz), 6.84 (1H, d, J=8.6 Hz), 7.14 (1H, dd, J=10.5, 16.9 Hz), 7.50 (1H, d, J=1.9 Hz), 7.59 (1H, dd, J=1.9, 8.6 Hz) EIMS (m/z): 392 (M$^+$)

Preparation 6

1,2-Bis(n-butoxycarbonylmethyloxy)-4-(3-oxo-1-propenyl)benzene

The compound (2.57 g) prepared in Preparation 4 was dissolved in dichloromethane (65 ml), manganese dioxide (5.66 g) was added thereto, and the mixture was stirred at room temperature for 24 hr. The reaction mixture was filtered through Celite, and the filtrate was concentrated. The residue thus obtained was subjected to the above procedure again, and then purified by column chromatography on silica gel (90 g, hexane:ethyl acetate=5:1) to give 1.82 g (yield 71%) of the title compound.

$^1$H-NMR (CDCl$_3$) δ: 0.91 (3H, t, J=7.5 Hz), 0.92 (3H, t, J=7.5 Hz), 1.29–1.41 (4H, m), 1.57–1.68 (4H, m), 4.20 (2H, t, J=6.7 Hz), 4.21 (2H, t, J=6.7 Hz), 4.78 (2H, s), 4.80 (2H, s), 5.88 (1H, dd, J=1.7, 10.5 Hz), 6.42 (1H, dd, J=1.7, 17.2 Hz), 6.87 (1H, d, J=8.6 Hz), 7.13 (1H, dd, J=10.5, 17.2 Hz), 7.54 (1H, d, J=1.9 Hz), 7.60 (1H, dd, J=1.9, 8.6 Hz) EIMS (m/z): 392 (M$^+$)

Preparation 7 n-Butyl 4-formylphenoxyacetate

The title compound (28.4 g, yield 99%) was prepared in the same manner as in Preparation 2, except that 4-hydroxybenzaldehyde (12.2 g) was used instead of 3,4-dihydroxybenzaldehyde.

$^1$H-NMR (CDCl$_3$) δ: 0.92 (3H, t, J=7.6 Hz), 1.30–1.40 (2H, m), 1.56–1.68 (2H, m), 4.23 (2H, t, J=6.9 Hz), 4.72 (2H, s), 7.01 (2H, d, J=8.8 Hz), 7.85 (2H, d, J=8.8 Hz), 9.91 (1H, s) SIMS (m/z): 237 (M$^+$+1)

Preparation 8 n-Butyl 4-(1-hydroxy-2-propenyl)phenoxyacetate

The compound (16.5 g) prepared in Preparation 7 was treated in the same manner as in Preparation 3 to give 8.82 g (yield 48%) of the title compound.

$^1$H-NMR (CDCl$_3$) δ: 0.92 (3H, t, J=7.4 Hz), 1.30–1.40 (2H, m), 1.58–1.68 (2H, m), 1.91 (1H, d, J=3.5 Hz), 4.21 (2H, t, J=6.7 Hz), 4.62 (2H, s), 5.14–5.19 (1H, m), 5.19 (1H, dt, J=1.3, 10.3 Hz), 5.33 (1H, dt, J=1.3, 17.2 Hz), 6.03 (1H, ddd, J=5.9, 10.3, 17.2 Hz), 6.89 (2H, d, J=8.7 Hz), 7.30 (2H, d, J=8.7 Hz) SIMS (m/z): 264 (M$^+$+1)

Preparation 9 n-Butyl 4-(1-oxo-2-propenyl)phenoxyacetate

The compound (8.80 g) prepared in Preparation 8 was treated in the same manner as in Preparation 6 to give 5.76 g (yield 66%) of the title compound.

$^1$H-NMR (CDCl$_3$) δ: 0.92 (3H, t, J=7.4 Hz), 1.30–1.40 (2H, m), 1.59–1.68 (2H, m), 4.22 (2H, t, J=6.7 Hz), 4.70 (2H, s), 5.89 (1H, dd, J=1.8, 10.5 Hz), 6.43 (1H, dd, J=1.8, 16.9 Hz), 6.97 (1H, d, J=9.0 Hz), 7.16 (1H, dd, J=10.5, 16.9 Hz), 7.96 (1H, d, J=9.0 Hz) EIMS (m/z): 262 (M$^+$)

EXAMPLE 1

[[4-[1,4-Dioxo-4-(4,5,6,7-tetrahydrothieno[3,2-c]pyridin-2-yl)butan-1-yl]-1,2-phenylene]dioxy]diacetic acid trifluoroacetate (a) The compound (491 mg) prepared in Preparation 5 and 5-t-butoxycarbonyl-2-formyl-4,5,6,7-tetrahydrothieno[3,2-c]pyridine (668 mg) were dissolved in 1,4-dioxane (12.5 ml), and 3-benzyl-5-(2-hydroxyethyl)-4-methyl-1,3-thiazolium chloride (101 mg) and triethylamine (105 μl) were further added thereto. The mixture was stirred at 80° to 90° C. for 21 hr. Chloroform was added to the reaction mixture, and the mixture was washed with 1N hydrochloric acid, water, a saturated aqueous solution of sodium hydrogencarbonate, and water in that order, and dried over magnesium sulfate. The solvent was then distilled off, and the residue was purified by column chromatography on silica gel (70 g, hexane:ethyl acetate=3:1) to give 464 mg of di-t-butyl [[4-[1,4-dioxo-4-(5-t-butoxycarbonyl-4,5,6,7-tetrahydrothieno[3,2-c]pyridin-2-yl)butan-1-yl]-1,2-phenylene]dioxy]diacetate (yield 54%).

$^1$H-NMR (CDCl$_3$) δ: 1.47 (9H, s), 1.48 (9H, s), 2.89 (2H, s), 3.31 (2H, t, J=5.8 Hz), 3.36 (2H, t, J=5.8 Hz), 3.73 (2H, s), 4.52 (2H, s), 4.64 (2H, s), 4.68 (2H, s), 6.82 (1H, d, J=8.6 Hz), 7.50 (1H, d, J=2.0 Hz), 7.53 (1H, s), 7.66 (1H, dd, J=2.0, 8.6 Hz) FDMS (m/z): 660 (M$^+$)

(b) Anisole (0.8 ml) and trifluoroacetic acid (3.2 ml) were added to the compound (288 mg) prepared in the above step (a), and the mixture was stirred at room temperature for 2.5 hr. Diisopropyl ether was added to the reaction mixture, and the resultant precipitate was collected by filtration to give 208 mg of the title compound (yield 85%).

$^1$H-NMR (DMSO-d6) δ: 3.11 (2H, t, J=6.1 Hz), 3.18–3.37 (4H, m), 3.46 (2H, t, J=6.1 Hz), 4.25 (2H, s), 4.76 (2H, s), 4.83 (2H, s), 7.00 (1H, d, J=8.8 Hz), 7.39 (1H, d, J=1.9 Hz), 7.67 (1H, dd, J=1.9, 8.8 Hz), 7.87 (1H, s), 9.16 (1H, br s), 13.02 (2H, br s) SIMS (m/z): 448 (M⁺+1)

EXAMPLE 2

Di-n-butyl [[4-[1,4-dioxo-4-(4,5,6,7-tetrahydrothieno [3,2-c]pyridin-2-yl)butan-1-yl]-1,2-phenylene]dioxy] diacetate hydrochloride (a) The procedure of Example 1 (a) was repeated, except that the compound prepared in Preparation 6 was used and, further, ethanol was used instead of 1,4-dioxane. Thus, 669 mg of di-n-butyl [[4-[1,4-dioxo-4-(5-t-butoxycarbonyl-4,5, 6,7-tetrahydrothieno[3,2-c]pyridin-2-yl)butan-1-yl]-1,2-phenylene]dioxy]diacetate was obtained (yield 68%).

¹H-NMR (CDCl₃) δ: 0.91 (3H, t, J=7.5 Hz), 0.92 (3H, t, J=7.5 Hz), 1.30–1.40 (4H, m), 1.50 (9H, s), 1.55–1.68 (4H, m), 2.89 (2H, s), 3.30 (2H, t, J=6.1 Hz), 3.36 (2H, t, J=6.1 Hz), 3.74 (2H, s), 4.20 (2H, t, J=6.6 Hz), 4.21 (2H, t, J=6.6 Hz), 4.52 (2H, s), 4.75 (2H, s), 4.79 (2H, s), 6.86 (1H, d, J=8.3 Hz), 7.53 (1H, s), 7.54 (1H, d, J=1.9 Hz), 7.67 (1H, dd, J=1.9, 8.3 Hz) FDMS (m/z): 659 (M⁺)

(b) Anisole (2 ml) and trifluoroacetic acid (8 ml) were added to the compound (669 mg) prepared in the step (a), and the mixture was stirred at room temperature for 2 hr. Chloroform (20 ml) and water (10 ml) were added to the reaction mixture, and the mixture was neutralized with sodium hydrogencarbonate and then separated into an organic layer and an aqueous layer. The aqueous layer was extracted with chloroform, and the extract was combined with the organic layer. The combined extract and organic layer were dried over magnesium sulfate, and the solvent was distilled off. The residue was purified by column chromatography on silica gel (40 g, chloroform:methanol= 40:1) to give an oil. The oil was dissolved in dioxane (25 ml), and the solution was stirred for 15 min while blowing hydrochloric acid gas into the system. The resultant crystals were collected by filtration, washed with ether, and lyophilized to give 528 mg of the title compound (yield 87%).

¹H-NMR (CDCl₃) δ: 0.91 (3H, t, J=7.4 Hz), 0.92 (3H, t, J=7.4 Hz), 1.30–1.40 (4H, m), 1.58–1.68 (4H, m), 3.21–3.32 (4H, m), 3.36 (2H, t, J=6.3 Hz), 3.52 (2H, br t, J=10.5 Hz), 4.19 (2H, t, J=6.7 Hz), 4.20 (2H, t, J=6.7 Hz), 4.33 (2H, s), 4.75 (2H, s), 4.78 (2H, s), 6.85 (1H, d, J=8.6 Hz), 7.52 (1H, d, J=2.0 Hz), 7.57 (1H, s), 7.64 (1H, dd, J=2.0, 8.6 Hz), 10.28 (1H, br s) SIMS (m/z): 560 (M⁺+1)

EXAMPLE 3

[[4-[4-(4-Amidinophenyl)-1,4-dioxobutan-1-yl]-1,2-phenylene]dioxy]diacetic acid trifluoroacetate (a) The procedure of Example 1 (a) was repeated, except that the compound prepared in Preparation 5 was used and 4-cyanobenzaldehyde was used instead of 5-t-butoxycarbonyl-2-formyl-4,5,6,7-tetrahydrothieno[3,2-c] pyridine. Thus, 285 mg of di-t-butyl [[4-[4-(4-cyanophenyl) -1,4-dioxobutan-1-yl]-1,2-phenylene]dioxy]diacetate was obtained (yield 54%).

¹H-NMR (CDCl₃) δ: 1.48 (18H, s), 3.38–3.47 (4H, m), 4.65 (2H, s), 4.68 (2H, s), 6.85 (1H, d, J=8.5 Hz), 7.51 (1H, d, J=1.8 Hz), 7.67 (1H, dd, J=1.8, 8.5 Hz), 7.79 (2H, d, J=8.2 Hz), 8.12 (2H, d, J=8.2 Hz) FDMS (m/z): 523 (M⁺)

(b) Pyridine (7 ml) and triethylamine (1.3 ml) were added to the compound (399 mg) prepared in the step (a), and the mixture was stirred for 30 min while blowing hydrogen sulfide gas under ice cooling into the system and further stirred at room temperature for 2 hr. The solvent was distilled off, and the resultant crystals were purified by recrystallization from CHCl₃ to give 357 mg of di-t-butyl [[4-[1,4-dioxo-4-(4-thiocarbamoylphenyl)butan-1-yl]-1,2-phenylene]dioxy]diacetate (yield 84%).

¹H-NMR (DMSO) δ: 1.42 (9H, s), 1.44 (9H, s), 3.33–3.42 (4H, m), 4.75 (2H, s), 4.81 (2H, s), 7.00 (1H, d, J=8.5 Hz), 7.42 (1H, d, J=1.8 Hz), 7.70 (1H, dd, J=1.8, 8.5 Hz), 7.96 (2H, d, J=8.5 Hz), 8.02 (2H, d, J=8.5 Hz), 9.68 (2H, br s) FDMS (m/z): 557 (M⁺)

(c) The compound (351 mg) prepared in the step (b) was dissolved in acetone (12 ml), methyl iodide (190 µl) was added thereto, the mixture was heated under reflux, and, 2.5 hr after the initiation of reflux, methyl iodide (95 µl) was further added thereof. Thereafter, the mixture was heated under reflux for 30 min, and the solvent was distilled off to give 553 mg of di-t-butyl [[4-[1,4-dioxo-4-[4-[(1-methylthio-1-imino)methyl]phenyl]butan-1-yl]-1,2-phenylene]dioxy]diacetate hydroiodide.

¹H-NMR (CDCl₃) δ: 1.48 (9H, s), 1.49 (9H, s), 2.64 (3H, s), 3.43 (4H, s), 4.65 (2H, s), 4.69 (2H, s), 6.86 (1H, d, J=8.8 Hz), 7.51 (1H, d, J=1.9 Hz), 7.69 (1H, dd, J=1.9, 8.8 Hz), 8.05 (2H, d, J=8.4 Hz), 8.14 (2H, d, J=8.4 Hz) SIMS (m/z): 572 (M⁺+1)

(d) The compound (547 mg) prepared in the step (c) was dissolved in methanol (12 ml), ammonium acetate (94.6 mg) was added thereto, and the mixture was heated under reflux for 3 hr. The solvent was distilled off, methylene chloride was added to the residue, insolubles were removed by filtration, and the filtrate was concentrated. Acetone and ether were added to the residue thus obtained, and the resultant crystals were collected by filtration to give 161 mg of di-t-butyl [[4-[4-(4-amidinophenyl)-1,4-dioxobutan-1-yl] -1,2-phenylene]dioxy]diacetate hydroiodide SIMS (m/z): 541 (M⁺+1).

(e) The compound (159 mg) prepared in the step (d) was treated in the same manner as in Example 1 (b) to give 112 mg of the title compound (yield from the compound prepared in the step (b): 34%).

¹H-NMR (DMSO) δ: 3.32–3.46 (4H, m), 4.71 (2H, s), 4.78 (2H, s), 6.99 (1H, d, J=8.8 Hz), 7.39 (1H, d, J=1.9 Hz), 7.69 (1H, dd, J=1.9, 8.8 Hz), 7.94 (2H, d, J=8.8 Hz), 8.18 (2H, d, J=8.8 Hz), 9.39 (2H, br s), 9.84 (2H, br s) FDMS (m/z): 429 (M⁺+1)

EXAMPLE 4

Di-n-butyl [[4-[4-(4-amidinophenyl)-1,4-dioxobutan-1-yl]-1,2-phenylene]dioxy]diacetate trifluoroacetate a) The procedure of Example 3 (a) was repeated, except that the compound (1.18 g) prepared in Reference Example 6 was used and ethanol was used instead of 1,4-dioxane. Thus, 1.22 g of di-n-butyl [[4-[4-(4-cyanophenyl)-1,4-dioxobutan-1-yl]-1,2-phenylene]dioxy]diacetate was obtained (yield 78%).

¹H-NMR (CDCl₃) δ: 0.91 (3H, t, J=7.3 Hz), 0.92 (3H, t, J=7.3 Hz), 1.30–1.41 (4H, m), 1.59–1.68 (4H, m), 3.37–3.46 (4H, m), 4.20 (2H, t, J=6.9 Hz), 4.21 (2H, t, J=6.9 Hz), 4.76 (2H, s), 4.80 (2H, s), 6.88 (1H, d, J=8.4 Hz), 7.55 (1H, d, J=1.9 Hz), 7.69 (1H, dd, J=1.9, 8.4 Hz), 7.80 (2H, d, J=8.8 Hz), 8.12 (2H, d, J=8.8 Hz) EIMS (m/z): 523 (M⁺)

(b) The compound (1.22 g) prepared in the step (a) was treated in the same manner as in Example 3 (b) to give 0.940 g of di-n-butyl [[4-[1,4-dioxy-4-(4-thiocarbamoylphenyl) butan-1-yl]-1,2-phenylene]dioxy]diacetate (yield 72%).

¹H-NMR (CDCl₃) δ: 0.91 (3H, t, J=7.3 Hz), 0.92 (3H, t, J=7.3 Hz), 1.30–1.41 (4H, m), 1.59–1.69 (4H, m), 3.40 (4H, s), 4.20 (2H, t, J=6.9 Hz), 4.22 (2H, t, J=6.9 Hz), 4.76 (2H, s), 4.80 (2H, s), 6.87 (1H, d, J=8.4 Hz), 7.54 (1H, d, J=1.9 Hz), 7.69 (1H, dd, J=1.9, 8.4 Hz), 7.93 (2H, d, J=8.0 Hz), 8.02 (2H, d, J=8.0 Hz) SIMS (m/z): 558 (M$^+$+1)

(c) The compound (0.940 g) prepared in the step (b) was treated in the same manner as in Example 3 (c) to give 1.36 g of di-n-butyl [[4-[1,4-dioxo-4-[4-[(1-methylthio-1-imino)methyl]phenyl]butan-1-yl]-1,2-phenylene]dioxy]diacetate hydroiodide.

$^1$H-NMR (CDCl$_3$) δ: 0.91 (3H, t, J=7.3 Hz), 0.92 (3H, t, J=7.3 Hz), 1.29–1.42 (4H, m), 1.60–1.69 (4H, m), 2.64 (3H, s), 3.42 (4H, s), 4.20 (2H, t, J=6.9 Hz), 4.21 (2H, t, J=6.9 Hz), 4.76 (2H, s), 4.80 (2H, s), 6.88 (1H, d, J=8.4 Hz), 7.54 (1H, d, J=1.9 Hz), 7.69 (1H, dd, J=1.9, 8.4 Hz), 8.18 (4H, s) SIMS (m/z): 572 (M$^+$+1)

(d) The compound (1.36 g) prepared in the step (c) was dissolved in methanol (17 ml), ammonium acetate (261 mg) was added thereto, and the mixture was heated under reflux for 1.5 hr. The solvent was distilled off, methylene chloride was added to the residue, insolubles were removed by filtration, and the filtrate was concentrated. The residue thus obtained was purified by column chromatography on silica gel (55 g, chloroform:methanol=15:1-methanol) to give 460 mg of di-n-butyl [[4-[4-(4-amidinophenyl)-1,4-dioxobutan-1-yl]-1,2-phenylene]dioxy]diacetate hydroiodide (yield from the compound prepared in the step (b): 41%).

$^1$H-NMR (CDCl$_3$) δ: 0.86 (3H, t, J=7.6 Hz), 0.90 (3H, t, J=7.6 Hz), 1.22–1.39 (4H, m), 1.53–1.67 (4H, m), 3.24 (4H, br s), 4.15 (2H, t, J=6.5 Hz), 4.18 (2H, t, J=6.5 Hz), 4.72 (2H, s), 4.75 (2H, s), 6.82 (1H, d, J=8.8 Hz), 7.46 (1H, s), 7.57 (1H, d, J=8.8 Hz), 7.95 (4H, s), 8.73–9.30 (3H, m) SIMS (m/z):

(e) The compound (369 mg) prepared in the step (d) was dissolved in dimethylformamide (7 ml), triethylamine (200 μl), di-t-butyl dicarbonate (165 μl), and 4-dimethylaminopyridine (8.3 mg) were added thereto, and the mixture was stirred at room temperature for one hr. Ethyl acetate was added to the reaction mixture, and the mixture was washed with 1N hydrochloric acid, water, a saturated aqueous solution of sodium hydrogencarbonate, and water in that order, and dried over magnesium sulfate. The solvent was then distilled off, and the residue was purified by column chromatography on silica gel (20 g, hexane:ethyl acetate=3:1–3:2) to give 280 mg of di-n-butyl [[4-[4-[N-(t-butoxycarbonyl)]amidinophenyl]-1,4-dioxobutan-1-yl]-1,2-phenylene]dioxy]diacetate hydroiodide (yield 64%).

$^1$H-NMR (CDCl$_3$) δ: 0.91 (3H, t, J=7.6 Hz), 0.92 (3H, t, J=7.6 Hz), 1.30–1.41 (4H, m), 1.56 (9H, s), 1.58–1.68 (4H, m), 3.37–3.47 (4H, m), 4.20 (2H, t, J=6.9 Hz), 4.21 (2H, t, J=6.9 Hz), 4.76 (2H, s), 4.80 (2H, s), 6.88 (1H, d, J=8.4 Hz), 7.55 (1H, d, J=1.9 Hz), 7.70 (1H, dd, J=1.9, 8.4 Hz), 7.96 (2H, d, J=8.4 Hz), 8.07 (2H, d, J=8.4 Hz) FDMS (m/z): 641 (M$^+$+1)

(f) Anisole (1.5 ml) and trifluoroacetic acid (6 ml) were added to the compound (275 mg) prepared in the step (e), and the mixture was stirred at room temperature for 3 hr. Diisopropyl ether was added to the reaction mixture, and the resultant crystals were collected by filtration. The crystals were then purified by reversed phase chromatography (Cosmoseal 75C$_{18}$-OPN=20 g, 0.2% aqueous trifluoroacetic acid solution:acetonitrile=7:3–1:1) and lyophilized to give 169 mg of the title compound (yield 60%).

$^1$H-NMR (CD$_3$OD) δ: 0.91 (3H, t, J=7.6 Hz), 0.94 (3H, t, J=7.6 Hz), 1.31–1.43 (4H, m), 1.59–1.69 (4H, m), 3.46 (4H, m), 4.20 (2H, t, J=6.5 Hz), 4.21 (2H, t, J=6.5 Hz), 4.83 (2H, s), 4.89 (2H, s), 7.05 (1H, d, J=8.4 Hz), 7.60 (1H, d, J=1.9 Hz), 7.77 (1H, dd, J=1.9, 8.4 Hz), 7.93 (2H, d, J=8.8 Hz), 8.24 (2H, d, J=8.8 Hz) SIMS (m/z): 541 (M$^+$+1)

EXAMPLE 5 n-Butyl 4-[4-(4-amidinophenyl)-1,4-dioxobutan-1-yl] phenoxyacetate hydroiodide (a) The procedure of Example 4 (a) was repeated, except that the compound (4.18 g) prepared in Reference Example 9 was used and ethanol and dimethylformamide (4:1) are used as the solvent. Thus, 3.35 g of n-butyl 4-[4-(4-cyanophenyl)-1,4-dioxobutan-1-yl]phenoxyacetate (yield 54%).

$^1$H-NMR (CDCl$_3$) δ: 0.92 (3H, t, J=7.4 Hz), 1.31–1.42 (2H, m), 1.60–1.69 (2H, m), 3.38–3.48 (4H, m), 4.22 (2H, t, J=6.7 Hz), 4.70 (2H, s), 6.96 (2H, d, J=9.0 Hz), 7.79 (2H, d, J=8.7 Hz), 8.01 (2H, d, J=9.0 Hz), 8.12 (2H, d, J=8.7 Hz) EIMS (m/z): 393 (M$^+$)

(b) The compound (3.23 g) prepared in the step (a) was treated in the same manner as in Example 3 (b) and recrystallized from ethyl acetate to give 2.07 g of n-butyl 4-[1,4-dioxo-4-(4-thiocarbamoylphenyl)butan-1-yl]phenoxyacetate (yield 59%).

$^1$H-NMR (CDCl$_3$) δ: 0.93 (3H, t, J=7.4 Hz), 1.31–1.41 (2H, m), 1.60–1.69 (2H, m), 3.43 (4H, s), 4.22 (2H, t, J=6.6 Hz), 4.70 (2H, s), 6.96 (2H, d, J=9.0 Hz), 7.94 (2H, d, J 9.0 Hz), 7.98–8.06 (4H, m)

(c) The compound (2.00 g) prepared in the step (b) was treated in the same manner as in Example 3 (c) to give 2.58 g of n-butyl 4-[1,4-dioxo-4-[4-[(1-methylthio-1-imino)methyl]phenyl]butan-1-yl]phenoxyacetate hydroiodide.

$^1$H-NMR (CDCl$_3$) δ: 0.93 (3H, t, J=7.6 Hz), 1.30–1.42 (2H, m), 1.60–1.69 (2H, m), 3.17 (3H, s), 3.39–3.47 (4H, m), 3.75 (1H, br s), 4.22 (2H, t, J=6.9 Hz), 4.70 (2H, s), 6.96 (2H, d, J=9.0 Hz), 8.00 (2H, d, J=9.0 Hz), 8.19 (4H, s) SIMS (m/z): 442 (M$^+$+1)

(d) The compound (2.45 g) prepared in the step (c) was treated in the same manner as in Example 4 (d) to give 2.21 g of the title compound (yield 88%).

$^1$H-NMR (DMSO-d6) δ: 0.87 (3H, t, J=7.4 Hz), 1.25–1.36 (2H, m), 1.52–1.62 (2H, m), 3.37–3.46 (4H, m), 4.13 (2H, t, J=6.6 Hz), 4.93 (2H, s), 7.06 (2H, d, J=9.0 Hz), 7.93 (2H, d, J=8.2 Hz), 7.99 (2H, d, J=9.0 Hz), 8.18 (2H, d, J=8.2 Hz) SIMS (m/z): 411 (M$^+$+1)

EXAMPLE 6

4-[4-(4-Amidinophenyl)-1,4-dioxobutan-1-yl] phenoxyacetic acid hydrochloride

The compound (108 mg) prepared in Example 5 (d) was suspended in ethanol (2 ml), 1N sodium hydroxide (420 μl) was added thereto, and the mixture was stirred at room temperature for 2.5 hr. The solvent was distilled off, and water (14 ml), 1N hydrochloric acid (0.84 ml), and dimethylformamide (2 ml) were added thereto, and the mixture was stirred at room temperature for 30 min. The solvent was distilled off, and chloroform was added to the residue. The resultant crystals were collected by filtration to give 60 mg of the title compound (yield 73%).

$^1$H-NMR (CF$_3$COOD) δ: 3.72 (4H, s), 4.96(2H, s), 7.14 (2H, d, J=8.8 Hz), 8.02 (2H, d, J=8.0 Hz), 8.15 (2H, d, J=8.8 Hz), 8.33 (2H, d, J=8.0 Hz) SIMS (m/z): 355 (M$^+$+1)

Pharmacological test: Inhibitory activity against platelet aggregation

The inhibitory activity of the compound according to the present invention against platelet aggregation was examined with human PRP (platelet rich plasma).

Nine volumes of a blood sample was taken out of the vein of a normal male human with a syringe in which one volume of a 3.8% sodium citrate solution was charged. The blood sample was centrifuged at 170×g at room temperature for 10 min. The supernatant thus obtained was isolated as PRP. The residual blood sample that PRP had been taken out was centrifuged at 2,700×g for 15 minutes. The supernatant was then taken as platelet poor plasma (PPP).

A platelet aggregation test was conducted with an agglignometer (PAM-8C, manufactured by MEBANICKS Co., Ltd.). Compounds under test were dissolved in a 50% DMSO saline, a 50% methanol saline, or physiological saline. The compound under test and PRP were preincubated for 2 min. An aggregation inducer ADP (CHRONO-PAR REAGENTS 384 ADP, CHRONO-LOG Corp.) was used in the form of a dilution with saline so that the final concentration is 5 µM.

The anti-platelet aggregation activity was determined as an inhibition rate to platelet aggregation effect of ADP in the absence of a compound under test as follows. The results are tabulated in Table 1.

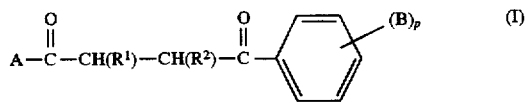

TABLE 1

| Example No. of Compound | IC$_{50}$ (µM) |
| --- | --- |
| 1 | 0.13 |
| 2 | 2.0 |
| 3 | 0.017 |
| 4 | 0.023 |
| 5 | 0.043 |
| 6 | <0.1 |

What is claimed is:

1. A γ-diketone compound represented by the following formula (I):

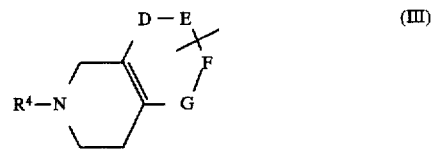

wherein

R$^1$ and R$^2$ which may be the same or different are hydrogen; lower alkyl in which at least one hydrogen atom optionally is replaced by hydroxyl, halogen, amino, carboxyl, lower alkoxy, lower alkylamino, or lower alkoxycarbonyl; phenyl in which at least one hydrogen atom of the phenyl optionally is replaced by hydroxyl, halogen, amino, carboxyl, lower alkoxy, lower alkylamino, lower alkoxycarbonyl, or halo-lower alkyl; or phenyl-lower alkyl in which at least one hydrogen atom of the phenyl optionally is replaced by hydroxyl, halogen, amino, carboxyl, lower alkoxy, lower alkylamino, lower alkoxycarbonyl, or halo-lower alkyl;

A is the following group (III):

(III)

D—E
     \\
      X
R$^4$—N        F
      \\   /
       —G

R$^4$ is hydrogen atom; lower alkyl in which at least one hydrogen atom may be substituted by hydroxyl, halogen, amino, or lower alkylamino; or amidino;

one of D and G is —S— and the other is a bond; E and F are CR5= where one R$^5$ represents hydrogen or lower alkyl and the other represents the bond linked to the rest of the molecule of formula (I);

B is —Z—(CH$_2$)$_q$COOR$^7$ wherein Z is —O— or a bond, R$^7$ is hydrogen, lower alkyl, or an ester residue which can be removed under physiological conditions and q is an integer of 1 to 4; and p is an integer of 1 to 3; or a pharmaceutically acceptable salt or solvate thereof.

2. The compound according to claim 1, wherein R$^1$ and R$^2$ are hydrogen.

3. The compound according to claim 2, wherein B is —Z—(CH$_2$)$_q$COOR$^7$.

4. The compound according to claim 1, which is [[4-[1,4-dioxo-4-(4,5,6,7-tetrahydrothieno[3,2-c]pyridine-2-yl)butan-1-yl]-1,2-phenylene]dioxy]diacetic acid.

5. The compound according to claim 1, which is di-n-butyl [[4-[1,4-dioxo-4-(4,5,6,7-tetrahydrothieno[3,2-c]pyridin-2-yl)butan-1-yl]-1,2-phenylene]dioxy]diacetate.

6. A pharmaceutical composition comprising an effective amount of the compound according to claim 1 or a pharmacologically acceptable salt or solvate thereof together with a pharmaceutically acceptable carrier.

7. A pharmaceutical composition according to claim 6 used for treatment of a thrombotic disease.

8. A method for treatment of a thrombotic disease, comprising the step of administering to mammals, an effective amount of the compound according to claim 1.

9. A method according to claim 8, wherein the mammal is a human being.

* * * * *